United States Patent
Jaffe et al.

(10) Patent No.: US 8,560,935 B2
(45) Date of Patent: Oct. 15, 2013

(54) SEGMENTING FORMS FOR MULTIPLE USER COMPLETION

(75) Inventors: Adam Jaffe, Mayfield Heights, OH (US); Sam Jaffe, Pepper Pike, OH (US)

(73) Assignee: American Sterling Dental Plan, LLC, Mayfield Heights, OH (US)

( * ) Notice: Subject to any disclaimer, the term of this patent is extended or adjusted under 35 U.S.C. 154(b) by 494 days.

(21) Appl. No.: 12/872,084

(22) Filed: Aug. 31, 2010

(65) Prior Publication Data

US 2012/0054592 A1 Mar. 1, 2012

(51) Int. Cl.
*G06F 17/00* (2006.01)
(52) U.S. Cl.
USPC .......................... 715/224; 715/221; 715/223
(58) Field of Classification Search
CPC ...................................... G06F 17/243
USPC ......................... 715/224, 221, 223
See application file for complete search history.

(56) References Cited

U.S. PATENT DOCUMENTS

| | | | |
|---|---|---|---|
| 7,409,632 B1 * | 8/2008 | DiRienzo | 715/226 |
| 7,983,934 B1 * | 7/2011 | Sholtis et al. | 705/2 |
| 2008/0255865 A1 * | 10/2008 | Ritter et al. | 705/1 |

OTHER PUBLICATIONS

Plasmeijer, et al., "iTasks: executable specifications of interactive work flow systems for the web", ICFP '07 Proceedings of the 12th ACM SIGPLAN international conference on Functional programming, pp. 141-152, ACM New York, NY, USA © 2007.*

* cited by examiner

*Primary Examiner* — Amelia Rutledge
(74) *Attorney, Agent, or Firm* — Hahn Loeser & Parks LLP; Carlos P. Garritano

(57) ABSTRACT

The claimed subject matter provides a system and/or a method that facilitates completing multiple electronic document applications. An interface component can receive two or more electronic documents, wherein each electronic document includes at least two or more questions with respective fill-in fields to be completed by a user input. A master field component can create a master field list that includes a first subset of questions and a second subset of questions and the first subset of questions is targeted toward a first user to answer and the second subset of questions are targeted toward second user to answer. A user segregation manager component can ensure an independent and secure log in to the master field list for each user to provide information. A form aggregation component can leverage the master field list to populate or update the electronic document.

20 Claims, 12 Drawing Sheets

SEGMENTING FORMS FOR MULTIPLE USER COMPLETION

BACKGROUND

Technological advances in computer hardware, software and networking have lead to increased demand for electronic information exchange rather than through conventional techniques such as paper correspondence, for example. Such electronic communication can provide split-second, reliable data transfer between essentially any two locations throughout the world. Many industries and consumers are leveraging such technology to improve efficiency and decrease cost through web-based (e.g., on-line) services. For example, consumers can purchase goods, review bank statements, research products and companies, obtain real-time stock quotes, download brochures, etc. with the click of a mouse and at the convenience of home.

Many entities (e.g., companies, businesses, colleges, foundations, groups, etc.) have an online presence which allows for the ease of access of information or the distribution of information. Such online presence can be a website, the use of email, chat applications, etc. and all can provide a direct and streamlined communication channel between the entity and users. For example, many entities utilize the online presence to distribute or enable access to digital or electronic materials such as forms, applications, brochures, pamphlets, and the like. In general, entities can provide cost effective and environmentally-safe alternatives via the online presence rather than using physical paper products.

In light of the above technological advances and conscience of being environmentally friendly, many industries employ electronic documents or digital documentation rather than the use of physical paper. Such electronic or digital formats have enabled flexibility in terms of ease of access, transferability, and readability. Moreover, the advent of digital or electronic documentation has simplified the filling out or completion of applications, forms, etc. Specifically, the electronic or digital documents can include fields or areas that can be completed by users with their specific information. For example, a company can provide a job application via a website, in which the job application can be a digital or electronic document (rather than a physical paper application) in which the user can access such digital or electronic document and fill out his or her information electronically.

SUMMARY

The following presents a simplified summary of the innovation in order to provide a basic understanding of some aspects described herein. This summary is not an extensive overview of the claimed subject matter. It is intended to neither identify key or critical elements of the claimed subject matter nor delineate the scope of the subject innovation. Its sole purpose is to present some concepts of the claimed subject matter in a simplified form as a prelude to the more detailed description that is presented later.

The subject innovation relates to systems and/or methods that facilitate updating and/or populating fill-in fields for an electronic document in which multiple users provide information or answers for the fill-in fields. In particular, an electronic document can be received via an interface and a master field component can segment questions (with respective fill-in fields for answers) to create a master field list. The master field list can include a set of questions from one or more electronic documents and can be segmented such that a first subset of questions are targeted for a first user or group of users and a second subset of questions are targeted for a second user or second group of users. The master field list can be managed by a user segregation manager component such that each user can independently and securely log in to the master field list in order to access and provide information for the respective subset of questions. In general, the master field lists enables each user or group of users to independently access and provide information or answers to the subset of questions the user or group of users is associated. A form aggregation component can leverage the master field list and the information collected in order to populate or update the fill-in fields associated with the electronic document. In other aspects of the claimed subject matter, methods are provided that facilitates enabling multiple user logging into an electronic document for secure and independent data collection for automatic generation of a filled-in electronic document.

The following description and the annexed drawings set forth in detail certain illustrative aspects of the claimed subject matter. These aspects are indicative, however, of but a few of the various ways in which the principles of the innovation may be employed and the claimed subject matter is intended to include all such aspects and their equivalents. Other advantages and novel features of the claimed subject matter will become apparent from the following detailed description of the innovation when considered in conjunction with the drawings.

DETAILED DESCRIPTION

Figure 1:
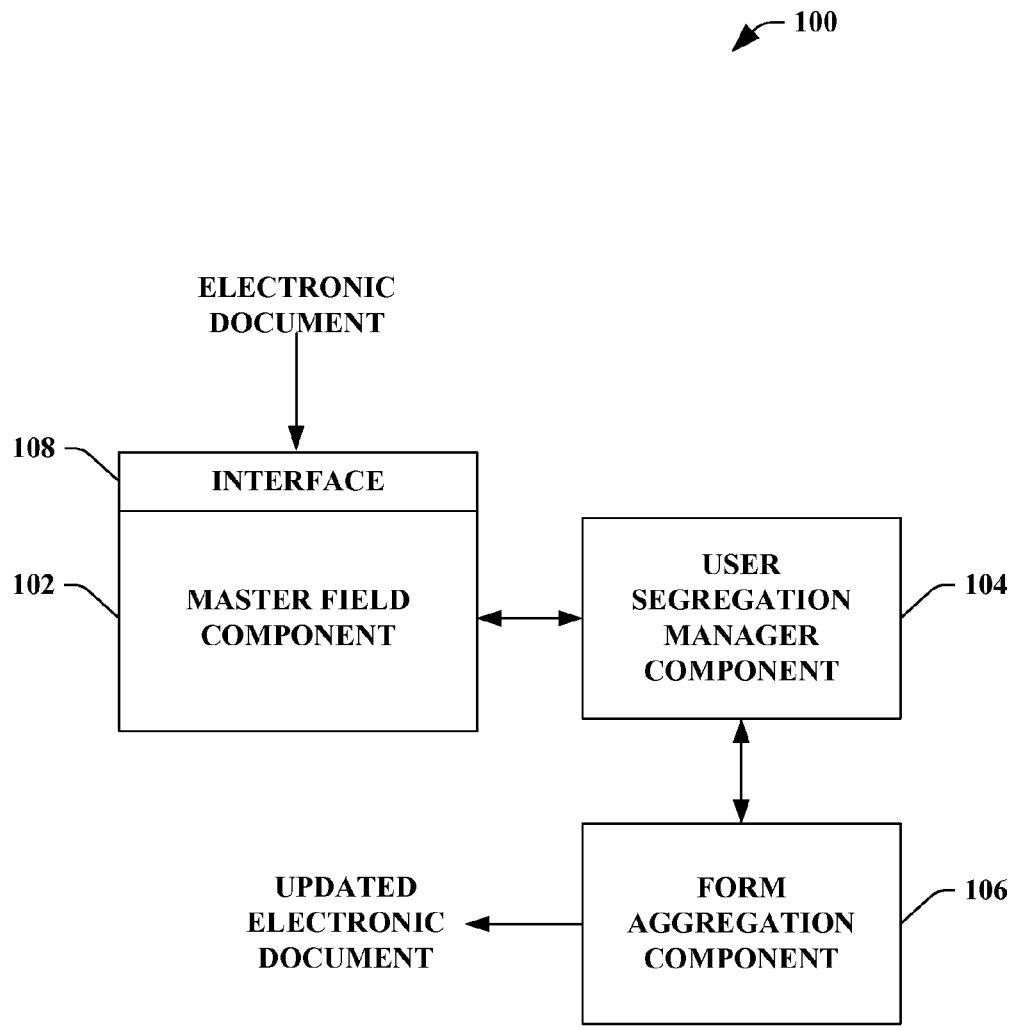
FIG. 1 illustrates a block diagram of an exemplary system that facilitates enabling multiple user logging into an electronic document for secure and independent data collection for automatic generation of a filled-in electronic document.

The claimed subject matter is described with reference to the drawings, wherein like reference numerals are used to refer to like elements throughout. In the following description, for purposes of explanation, numerous specific details are set forth in order to provide a thorough understanding of the subject innovation. It may be evident, however, that the claimed subject matter may be practiced without these specific details. In other instances, well-known structures and devices are shown in block diagram form in order to facilitate describing the subject innovation.

As utilized herein, terms "component," "system," "interface," "engine," "processor," "module," "cloud," and the like are intended to refer to a computer-related entity, either hardware, software (e.g., in execution), and/or firmware. For example, a component can be a process running on a processor, a processor, an object, an executable, a program, a function, a library, a subroutine, and/or a computer or a combination of software and hardware. By way of illustration, both an application running on a server and the server can be a component. One or more components can reside within a process and a component can be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope or spirit of the claimed subject matter. Moreover, the word "exemplary" is used herein to mean serving as an example, instance, or illustration. Any aspect or design described herein as "exemplary" is not necessarily to be construed as preferred or advantageous over other aspects or designs.

Now turning to the figures, FIG. 1 illustrates a system 100 that facilitates enabling multiple user logging into an electronic document for secure and independent data collection for automatic generation of a filled-in electronic document. The system 100 can include a master field component 102 that can receive an electronic document or digital document via an interface component 108, wherein the electronic document or digital document can include a set of questions that can each include a respective field for a fill-in answer or information. The master field component 102 can segregate the set of questions from the electronic document into two or more subsets, wherein each subset is targeted to a particular user based on the answers that are to be provided, the content of the question, or who is able to provide the answer to the question (s). In general, the master field component 102 can create a master field list that can include the segregated subsets of questions from the electronic document. Moreover, the master field list can enable a multiple user log in into the master field list in which each user can independently and separately access and provide information for a respective subset of questions.

The system 100 can also include a user segregation manager component 104 that manages user log in and security for the master field list. The master field list created allows for two or more users to interact with respective subsets of questions in order to independently provide information for the electronic document. The system can further include a form aggregation component 106 that can leverage the master field list to collect information received from the first user related to the first subset of questions and information received from the second user related to the second subset of questions to update the set of questions and the respective set of fill-in fields on the electronic document. Specifically, the form aggregation component 106 can utilize the master field list and the information independently collected from the multiple users to populate or update at least one electronic document and respective fill-in fields. In general, the system 100 can automatically update or populate one or more electronic documents utilizing a master field list that enables multiple users log in to answer subset of questions independently and secure.

The master field component 102 can separate or segment the set of questions from one or more electronic documents into two or more subsets of questions. In other words, a set of questions can be segregated into a first subset of questions and a second subset of questions, wherein the first subset of questions are targeted for a first user and the second subset of questions are targeted for a second user. The master field list can enable the first user to log in independent of other users in order to interact (e.g., access, provide information, etc.) with the first subset of questions. Similarly, the master field list can enable the second user to log in independent of other users in order to interact with the second subset of questions.

By utilizing a master field list created for the one or more electronic documents, the filling out or completion of such electronic documents can be mitigated and optimized. For instance, the electronic documents can be applications or forms that are to be completed in which each electronic document can include similar sets of questions. Additionally, the master field list can enable two or more users to independently and separately provide information for respective subset of questions. By enabling multiple users to independently log in into the master field list to provide answers to respective subset of questions, the electronic documents can be completed or updated efficiently. Conventional techniques typically require each user to manually and tediously answer questions in each of the electronic documents-which can be time consuming, repetitive, and also insecure since information provided by each user for the electronic documents can be visible during the filling out process.

The user segregation manager component 104 can enforce security techniques in order to allow each user to access specific subsets of questions in order to ensure each user can independently (e.g., independent from other users that log in into the master field list) provide information for the fill-in fields for the respective subset of questions for the electronic documents. For instance, the user segregation manager component 104 can ensure that a first user can log into the master field list to provide information for a first subset of questions (segmented and targeted for the first user) and that a second user can log into the master field list to provide information for a second subset of questions (segmented and targeted for the second user), wherein each log in into the master field list for each the first user and the second user is secure and separate to ensure privacy of any information provided for questions within the electronic document.

The form aggregation component 106 can tabulate or collect information from the master field list in order to populate or update fill-in fields on the electronic document(s). Based on the master field list collecting information from two or more users via the two or more respective subsets of questions, the form aggregation component 106 can leverage the information collected to complete, fill-out, or update the at least one electronic document. It is to be appreciated that the updated or populated electronic document using the information from the master field list can be outputted in an electronic format, physical format (e.g., paper, print out, etc.), and/or any combination thereof.

For example, the electronic document can be any digital or electronic document that includes questions and respective fill-in fields that are to be completed. It is to be appreciated that the electronic or digital document can be in any format (e.g., image, PDF, word processing application format, scanned format, etc.). For instance, the electronic document can be an electronic application, a digital form, an electronic questionnaire, a college application, a business application for credit at a bank, a credentialing application for a medical practice, a credentialing application for a dental practice, a business lease agreement, a credit card application for a business, a group medical insurance application for a business, a loan application, a student loan application, an electronic evaluation form, etc. For instance, the electronic document can be a region-based credentialing application from at least one of a medical insurance company or a dental insurance company. Moreover, the electronic document can be a region-based credentialing application from at least one of a medical insurance company or a dental insurance company, wherein 1) the medical insurance company provides insurance coverage to a patient in which such region-based credentialing application enables a medical physician to accept such insurance coverage for patients, and 2) the dental insurance company provides insurance coverage to a patient in which such region-based credentialing application enables a dental physician to accept such insurance coverage for patients.

Additionally, the electronic document can be segregated into two or more subsets of questions for specific users when the electronic document includes a set of questions that can be answered or completed by two or more users based on each user's capability or knowledge of answering such set of questions, the type of questions, or what the question is asking. For instance, the electronic document can be targeted to an entity in which the entity can include two or more users that can provide answers or information for the questions and respective fill-in fields. For instance, the entity can be a business, a law firm, a medical practice, a dental practice, a household, a family unit, and the like. As discussed, the set of questions from the electronic document(s) can be segregated into two or more subset of questions targeted for particular users, wherein the particular users can be as follows: an administrative user and at least one medical professional user; a first parent and a second parent; at least one parent user and at least one child user; a professional user and a professional assistant user; a teacher user and a student user; a professor user and a student user; a borrower user and a co-signer user; etc.

For example, a law firm can apply for insurance from various companies, wherein each insurance company can include electronic applications with sets of questions that may overlap between each electronic application. Moreover, within the law firm, there can be at least two groups of users identified that have knowledge to answer the questions within the electronic application. For instance, the first users can be attorneys and the second users can be administrative users (e.g., administrative assistant, office manager, etc.). Based on these two user groups, the totality of questions within the various electronic applications for each insurance company can be segmented and partitioned to create a master field list with a first subset of questions targeted to the attorneys and a second subset of questions targeted to the administrative users. The master field list can enable the first group of users to securely log in into the master field list to access and/or provide information for the first subset of questions. Moreover, the master field list can enable the second group of users to securely log into the master field list to access and/or provide information for the second subset of questions, wherein the users from the second group and the users from the first group are secured and independent from one another (e.g., a user in the first group of users is limited to provide information (e.g., answers) to the first subset of questions and a user in the second group is limited to provide information (e.g., answers) to the second subset of questions. Upon collecting the information from the first group of users and the second group of users, the master field list can be leveraged to populate and/or update the electronic insurance applications. By utilizing the independent and secure master field list multiple user log in, the electronic documents can be filled-out efficiently and completion of such forms can be optimized.

In addition, the system 100 can include any suitable and/or necessary interface component 108 (herein referred to as "interface 108"), which provides various adapters, connectors, channels, communication paths, etc. to integrate the master field component 102 into virtually any operating and/or database system(s) and/or with one another. In addition, the interface component 108 can provide various adapters, connectors, channels, communication paths, etc., that provide for interaction with the master field component 102, the user segregation manager component 104, the form aggregation component 106, and any other device and/or component associated with the system 100.

Figure 2:
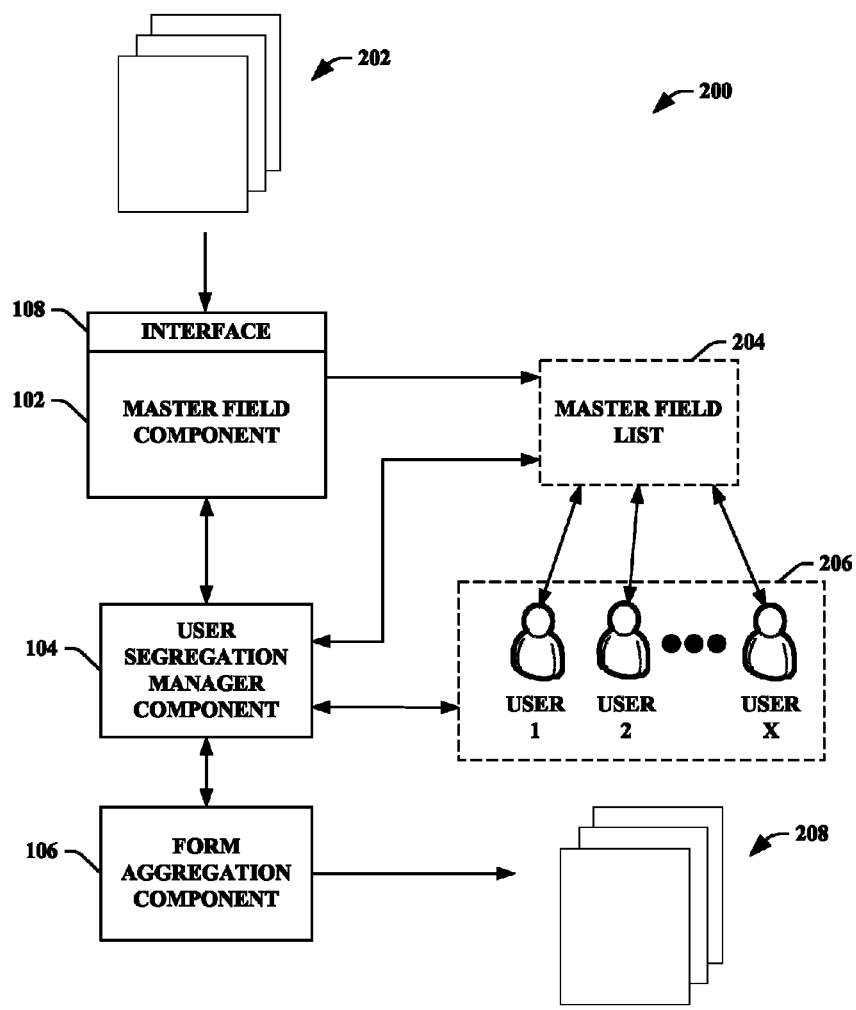
FIG. 2 illustrates a block diagram of an exemplary system that utilizes a master field list to collect information from independently logged in multiple users in order to receive answers for an electronic document.

FIG. 2 illustrates a system 200 that facilitates utilizing a master field list to collect information from independently logged in multiple users in order to receive answers for an electronic document. The system 200 can include the interface 108 that can receive at least one electronic document or physical document that has been converted to an electronic document (e.g., utilizing a scanning technique, a copy technique, a paperless system, a scanner, a photocopy machine, etc.). In other words, the interface 108 can receive any suitable document in electronic format in which the electronic document includes at least one fill-in field associated with a question, wherein the fill-in field is to be completed or filled in with an answer to such question. It is to be appreciated that the interface 108 can receive one or more electronic documents that each include fill-in fields for each respective set of questions within each electronic document. For example, a first electronic document can include a first set of questions with respective fill-in fields for such questions and a second electronic document can include a second set of questions with respective fill-in fields for such questions. Overall, the system 200 can utilize any suitable number of electronic documents in which each electronic document can include any suitable number of questions with respective fill-in fields for answers to such questions. The electronic document can be any suitable electronic document that includes at least two or more questions with respective fill-in fields to receive or store answers to such questions. The electronic document can be, but is not limited to, an electronic application, a digital form, an electronic questionnaire, a college application, a business application for credit at a bank, a credentialing application for a medical practice, a credentialing application for a dental practice, a business lease agreement, a credit card application for a business, a group medical insurance application for a business, a loan application, a student loan application, an electronic evaluation form, etc.

The electronic documents received via the interface 108 can be evaluated by the master field component 102 in order to create a master field list 204. The master field list 204 can include a totality of questions associated with the one or more electronic documents in which the master field list segments the totality of questions into subset of questions. The master field component 102 can segment or separate the questions based upon the target user that is to answer the questions, the type of question, or the user that has the knowledge to answer the question. In general, the master field list 204 can enable at least two or more users 206 (e.g., also referred to as users 206) to securely and independently log in to the master field list 204 in order to provide information for each respective subset of questions. It is to be appreciated that the users 206 can include user 1, user 2, to user X, where X is a positive integer. In other words, the questions can be evaluated and segmented into two or more subsets of questions such that a first subset of questions can be created within the master field list 204 for a first user or a first group of users and a second subset of questions can be created within the master field list 204 for a second user or a second group of users. It is to be appreciated that the master field list 204 can create any suitable number of subsets of questions from the electronic documents targeted for any suitable number of users or groups of users.

The master field list 204 can ensure a secure and independent channel for interaction with the subset of questions for each user or group of users. In other words, if a user is identified as to be answering a first subset of questions, that user can securely access such subset of questions without interfering with any other user or subset of questions. Moreover, each user can be associated to a subset of questions from the set(s) of questions from the at least one electronic document in which each user can include his or her own security level or clearance. For instance, a user can have a security level that enables at least one of the following: access to the subset of questions; answer to the subset of questions (e.g., provide information to a question, etc.); modify or edit answer(s) for a question within the subset of questions; and review of answer(s) for a question within the subset of questions.

In a general example, the master field list 204 can be created such that the totality of questions included within the one or more electronic documents can be segmented into subsets of questions, wherein each subset is targeted for a particular user or group of users. Within the master field list, each user can provide information or access information securely and independently from one another (e.g., each user can log in to the master field list 204 and establish a secure channel, etc.). For instance, there can be user A, user B, and user C, wherein user A is assigned or associated with a subset of questions A, user B is assigned or associated with a subset of questions B, and user C is assigned or associated with a subset of questions C. In one example in which each user is independently secure from one another, the following can be employed: user A can have access to view and/or answer solely the subset of questions A in which user B and user C cannot access or provide answers to subset of questions A; user B can have access to view and/or answer solely the subset of questions B in which user A and user C cannot access or provide answers to subset of questions B; and user C can have access to view and/or answer solely the subset of questions C in which user A and user B cannot access or provide answers to the subset of questions C. In general, it is to be appreciated that the system 200 can enable a security level for each user or group of users that have an associated or associated subset of questions within the master field list 204.

Following the example above, each user can have a security level for an associated subset of questions and a disparate subset of questions. For instance, user A can access and provide information for subset of questions A and also be able to access or review subset of questions B related to user B or subset of questions C related to user C. Thus, user A can review or monitor the answers provided for subset of questions B and subset of questions C. It is to be appreciated that such reviewing or monitoring security level can be included for any suitable user or group of users associated with a subset of questions (e.g., user A can review or monitor subset of questions B or subset of questions C, user B can review or monitor subset of questions A or subset of questions C, user C can review or monitor subset of questions A or subset of questions B, etc.).

For instance, an electronic document can be a college application that can be segmented into a first subset of questions for a parent and a second subset of questions for a child or minor. The master field list 204 can be created to include such subsets of questions and enable the parent to log in and access and provide answers to the corresponding subset of questions for the parent. Moreover, the child can log in and access and provide answers to the corresponding subset of questions for the child. It is to be appreciated that the master field list enables each user (e.g., child and parent in this example) to independently log in and access and/or provide answers for the respective subset of questions. Following this example, an additional child can log in to the master field list and access and/or provide answers to the second subset of questions based on his or her identified role or association to a subset of questions. It is to be appreciated that the additional child can log in and provide answers to his or her respective questions with his or her specific information. In other words, there can be questions from the electronic document segmented into the master field list that each child that logs in can fill-out independently. Additionally, the parent can have a review or monitor security level that enables review or monitoring of the answers provided by the child or children.

The form aggregation component 106 can tabulate or collect the information collected from the users 206 via the master field list 204 in order to update or populate the at least electronic document 208 to create the updated or populated electronic document 208 that includes answers for the fill-in fields. In other words, the populated or updated electronic document 208 can include information collected from the master field list 204 (and in turn, from each user that independently logged in to the master field list 204 to provide secure information). Thus, the fill-in fields associated with multiple electronic documents can be updated or populated by leveraging the master field list in order to create the updated or populated electronic document 208.

For example, there can be a first credentialing application A and as second credentialing application B. Credentialing application A can have a set of questions with respective fill-in field for answers and credentialing application B can have a set of questions with respective fill-in fields for answers. Although credentialing application A and credentialing application B are different applications for different insurance companies, there can be substantially similar questions between the two credentialing applications. Such questions can be segmented into a master field list in which questions can be partitioned or separated into at least two subsets. For instance, the first subset of questions can be from credentialing application A and B and can be targeted for a first user or group of users (e.g., an administrator user, a parent user, a borrower user, etc.), while the second subset of questions can be from credentialing application A and B and can be targeted for a second user or group of users (e.g., a physician user, a child user, a co-signer user, etc.). In general, the sets of questions from the credentialing applications A and B can be segmented into a first subset of questions that is targeted to a specific first user or first group of users and a second subset of questions that is targeted to a specific second user or second group of users.

For instance, in a credentialing application, the set of questions can be segmented into a first subset of questions for an administrator user and a second subset of questions for a physician user (e.g., medical doctor, dentist, etc.). This can allow a physician user to provide answers for questions to which he or she would know the answers separately and securely from an administrator user. On the other hand, this can allow the administrator user to provide answers for questions to which he or she would know the answers separately and securely from a physician user. This can optimize the filling out of the credentialing application(s). For instance, the physician user can access solely the questions within his or her subset and will not be distracted or confused by questions that he or she may not understand or know the answers. Similarly, an administrator user can access solely the questions within his or her subset and will not be confused or distracted by questions that are targeted for a physician user. Moreover, it is to be appreciated that there can be any suitable number of physician users and/or administrator users that can log in to the master field list to complete his or her respective set of questions in order to enable an update or a population of the credentialing application via the master field list.

In general, an administer user can be any user that has knowledge about a business practice, medical practice, or dental practice such as, but not limited to, office location, credentialing application contact information, staff or business office contact information, billing information, payment information, accessibility of the office information, services for the office, insurance information, professional liability insurance information, information not known to a physician user, etc. A physician user can be any user that has knowledge about his or her education or employment history such as, but not limited to resume information, medical/dental expertise, employers, professional identifications, board certifications, state licenses, training information, internship/residency information, fellowship information, specialty information, certifications, office hours of work, partners/associates, mid-level practitioners, hospital privileges, disclosure questions, etc.

For example, the questions within the first subset of questions for the administrator user can be, but are not limited to, primary credentialing contact (e.g., first name, last name, address, email address, phone, fax, etc.), practice location information (e.g., physician group, practice name, group or corporate name as it appears on W-9, group tax identification number, etc.), office manager or business office staff contact information (e.g., first name, last name, telephone, fax, email address, etc.), billing contact information (e.g., first name, last name, address, telephone, fax, email, etc.), payment and remittance information (e.g., electronic billing information, billing department, who to make checks payable to, first name, last name, address, phone, fax, email address, etc.), office hour information (e.g., phone coverage duration, after hours back office telephone, answering service information, voice mail information, etc.), open practice status (e.g., accepting new patients into the practice, accepting existing patients with change of payor, accepting new patients with physician referral, accepting all new patients, accepting new Medicare patients, accepting new Medicaid patients, variations by plan explanations, practice limitations, age limitations, maximum age, minimum age, other limitations, etc.), language information (e.g., non-English languages spoken by office personnel, language codes, interpreters, languages interpreted, language code for languages interpreted, etc.), accessibility information (e.g., meeting ADA accessibility requirements, offering handicapped access to building, offering handicapped access to parking, offering handicapped access to restroom, offering services to the disabled, offering text telephony (TTY), offering American Sign Language, offering mental/physical impairment services, accessibility by public transportation, accessible by bus, accessible by subway, accessible by regional train, other handicapped access, other disability services, other transportation access, etc.), services information (e.g., laboratory services, accrediting/certifying program for laboratory services, radiology services, X-ray certification type, EKGs, drawing blood, asthma treatment, pulmonary function testing, allergy injections, age appropriate immunizations, osteopathic manipulation, physical therapy, allergy skin testing, flexible sigmoioscopy, N hydration treatment, care of minor lacerations, routine office gynecology, pelvic/PAP, tympanometry/audiometry screening, cardiac stress test, anesthesia administered in the office, class or category of anesthesia administered, name of administer of anesthesia, type of practice, additional office procedures provided, etc.), professional liability insurance carrier information (e.g., carrier or self-insured name, address of carrier or self-insured name, original effective date of carrier or self-insured name, effective date of carrier or self-insured name, expiration date of carrier or self-insured name, type of coverage, amount of coverage per occurrence, amount of coverage aggregate, policy includes tail coverage, policy number, etc.), current professional liability insurance carrier information, future professional liability insurance carrier information, previous professional liability insurance carrier information, etc.

For example, the questions within the second subset of question for the physician user can be, but are not limited to, full name (e.g., first name, middle name, last name, suffix, previous names, etc.), city of birth, date of birth, state of birth, country of birth, social security number, foreign national identification number (FNIN), FNIN country of issue, languages spoken that are non-English, home address, (e.g., number, street, apartment number, city, state, zip code, telephone, etc.), email address, fax number, preferred method of contact (e.g., mail, email, fax, etc.), professional identification information (e.g., Federal Drug Enforcement Agency (FDEA) number, FDEA issue date, FDEA state of registration, FDEA expiration, etc.), Controlled Dangerous Substance (CDS) certificate information (e.g., CDS certificate number, CDS issue date, CDS state of registration, CDS expiration date, etc.), state license number, license issuing date, license issuing date, license state code, license type, license expiration date, Medicare and/or Medicaid information (e.g., Medicare provider, Medicare number, UPIN, Medicaid provider, Medicaid number, Medicaid state, National Provider Identification (NPI) number, USMLE number, worker compensation number, ECFMG number, ECFMG certificate issue date, undergraduate information (e.g., undergraduate school, undergraduate address, city, state, country, zip code, telephone, fax, start date, end date, degree awarded, etc.), graduate school information (e.g., graduate type, graduate school code, graduate school name, start date, end date, degree awarded, graduate school address, country, postal code, etc.), education and training information (e.g., institution name, hospital name, school code if affiliated with medical school, address, internship information, residency information, fellowship information, department or specialty information for an internship, department or specialty information for a residency, department or specialty information for a fellowship, start date or end date for an internship, start date or end date for a residency, start date or end date for a fellowship, name of director for education or training, etc.), professional and medical specialty information (e.g., specialty code, initial certification date, board certified, certifying board code, recertification date, expiration date, directory listing for HMO, directory listing for PPO, directory listing for POS, etc.), certifications for professional and medical specialty information (e.g., basic life support, expiration of certification for basic life support, CPR, expiration of certification for CPR, advanced cardiac life support, expiration of certificate for advanced cardiac life support, neonatal advanced life support, expiration of certificate for neonatal advanced life support, advanced life support in OB, expiration of certificate for advanced life support in OB, advanced trauma life support, expiration of certificate for advanced trauma life support, pediatric advanced life support, expiration of certificate for pediatric advanced life support, etc.), practice interests, practice location information (e.g., start date at practice, address, telephone, fax, email address, individual tax identification, office hours for week, etc.), mid-level practitioner information (e.g., practitioner first and last name, practitioner license number, practitioner certificate number, practitioner state, practitioner type, etc.), partners or associate information (e.g., first and last name of partner/associate, specialty code for partner/associate, covering colleague, provider type, etc.), covering colleague information (e.g., list of covering colleagues that are not partners/associates at the practice, first and last name of covering colleagues, specialty code of covering colleagues, provider type, etc.), admitting arrangements (e.g., hospital privileges, admitting arrangements for patients, etc.), hospital privileges (e.g., primary hospital information, primary hospital name, primary hospital address, primary hospital department name, primary hospital department director name, primary hospital affiliation start date, primary hospital affiliation end date, admitting privilege status for primary hospital, other hospital affiliations, etc.), military duty or work history information (e.g., work history, practice or employer name, address for previous practice or employer, telephone, fax, reason for departure, etc.), gaps in professional or work history information (e.g., gap start date, gap end date, explanation for gap, etc.), professional references (e.g., name, address, telephone, fax, email, etc.), disclosure questions (e.g., related to licensure, related to hospital privileges and other affiliations, related to education, related to training, related to board certification, related to DEA or state controlled substance registration, related to Medicare, related to Medicaid, related to other governmental program participation, related to other sanctions, related to investigations, related to malpractice claims history, related to criminal history, related to civil history, related to ability to perform job, etc.), standard authorization, attestation, and release, etc.

Figure 3:
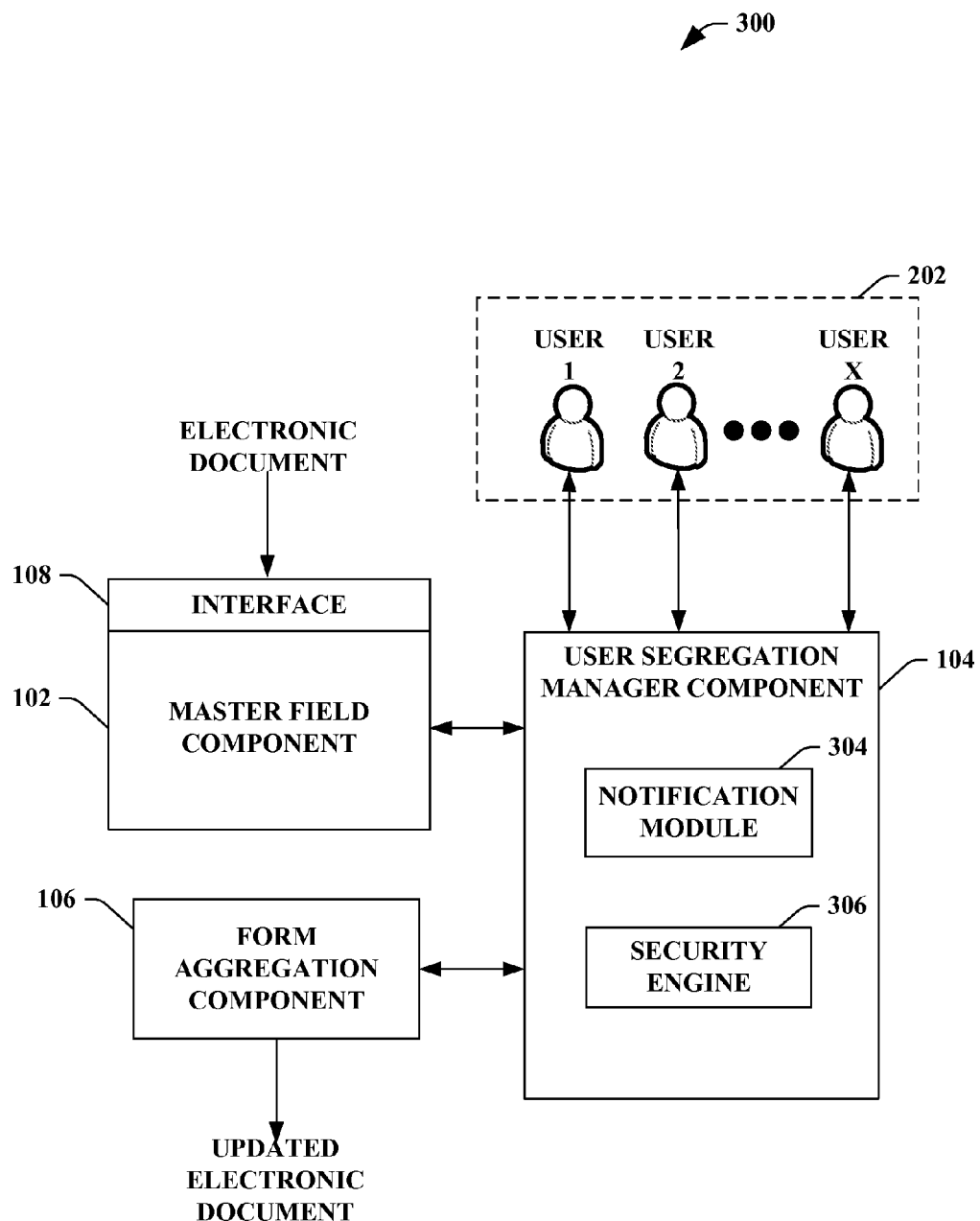
FIG. 3 illustrates a block diagram of an exemplary system that facilitates monitoring and securing a progress related to an electronic document that is to be completed by multiple users having respective questions from the electronic document to provide information.

FIG. 3 illustrates a system 300 that facilitates monitoring and securing a progress related to an electronic document that is to be completed by multiple users having respective questions from the electronic document to provide information. An electronic document can be received via the interface 108, wherein the electronic document can include at least two questions with respective fill-in fields for answers. The master field component 102 can evaluate the electronic document and create a master field list that includes the set of questions from the electronic document. The master field component 102 can segment the at least two questions into a first subset of questions and a second subset of questions in which the first subset of questions is targeted for a first user or first group of users and the second subset of questions is targeted for a second user or second group of users. It is to be appreciated that the segmented subset of questions are targeted to user(s) based upon the type of question, the answer that is to be provided to the question, and/or who can answer the question. The master field list can enable multiple users to log in and provide information or answers to the subset of questions in a secure and independent manner. In general, the user segregation manager component 104 can manage the log in and information or answer collection for the users 202. For instance, the user segregation manager component 104 can enforce security levels and profiles such that each user can access or provide answers to the associated subset of questions. For instance, user A can access and provide answers to a first subset of questions A independently and securely, while user B can access and provide answers to a second subset of questions B independently and securely. Moreover, user C can be associated with the second subset of questions and can securely and independently answer the second subset of questions with his or her information. Upon collection of information from the users 202, the form aggregation component 106 can update or populate the electronic document and fill-in fields with the data stored within the master field list in order to provide an updated or populated electronic document.

The user segregation manager component 104 can further include a notification module 304. The notification module 304 can provide notifications in regards to a status or progress of updating the master field list and/or the electronic document. For instance, the notification module 304 can communicate a notification to a user based upon his or her progress of providing information or answers to a master field list. In another example, the notification module 304 can communicate a notification when a master field list is available to access to receive information. For example, the notification module 304 can communicate a notification, wherein the notification can be an email, a short message service (SMS), a text message, a phone call, a video call, a cellular call, a page, a message to a social network, a message to a website, a message to an automated telephone service, etc. Moreover, the notification can be configured to be communicated to a user based upon a predefined progress of completion of the subset of questions (e.g., notification sent after completing five of fifteen questions, etc.) or duration of time (e.g., notification sent after three days from availability of master field list, etc.). For instance, a notification can be communicated upon the completion of his or her subset of questions. In another example, the notification can be communicated when the user provides information for 50% of the subset of questions. It is to be appreciated that the notification can be defined to be communicated with any percentage of completing the subset of questions. Moreover, the notification module 304 can communicate notifications to a first user associated with the first subset of questions and a second user associated with the second subset of questions. In particular, a user that has security level or privileges for access or review (e.g., no security for providing answers to questions) can receive notifications based on other users' progress of completion. Additionally, the security engine 306 can enable manual configuration for the communication of notifications based on specific preferences (e.g., notifications sent based upon deadlines, user schedule, user calendar, appointments, work hours, etc.).

The user segregation manager component 104 can further include a security engine 306. The security engine 306 can ensure secure data communication in regards to the master field list and any data exchange therewith. The security engine 306 can utilize security levels with defined characteristics. For instance, a security level can be associated with a first subset of questions that enables access to the master field list and input to the master field list for the first subset of questions. In another example, the security level can be associated with the first subset of questions and a second subset of questions in which access or review of the subset of questions and answers can be enabled. In general, the security engine 306 can utilize a username and password for each user that is to log in to the master field list. For instance, a user can log in to a website with a username and password to access a master field list that includes his or her subset of questions to answer.

Figure 4:
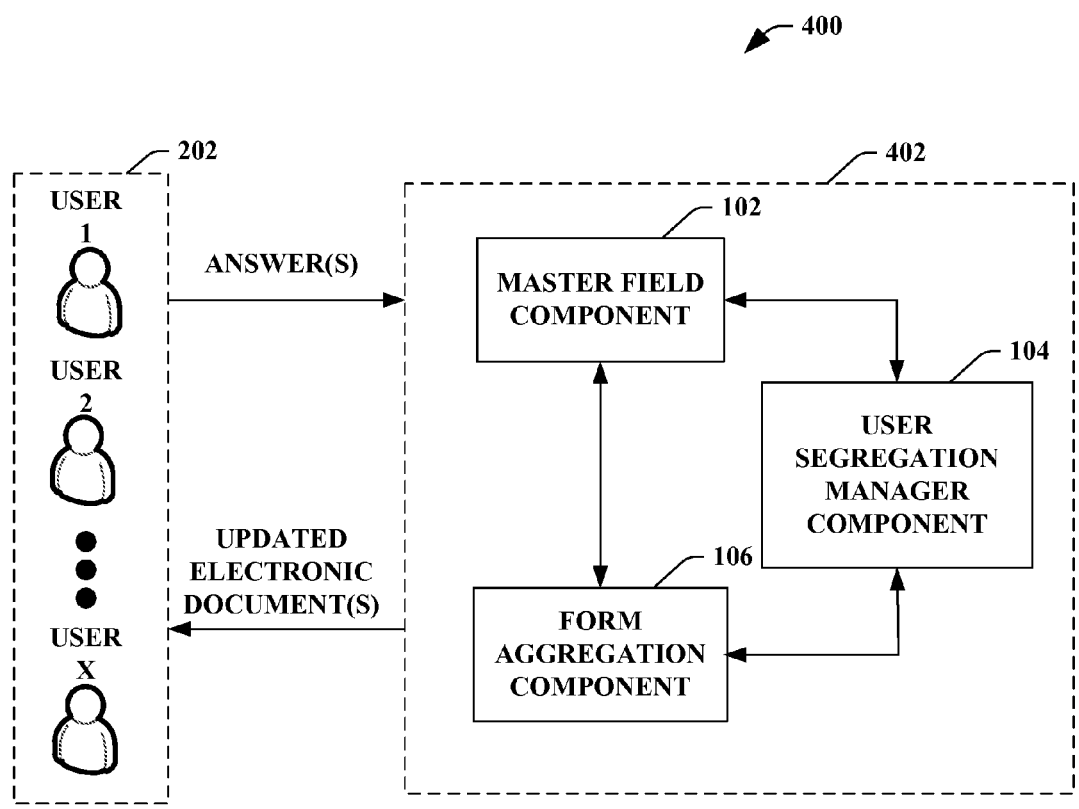
FIG. 4 illustrates a block diagram of an exemplary system that facilitates collecting information from two or more users to update at least one electronic document utilizing a multiple user independent logging in technique.

FIG. 4 illustrates a system 400 that facilitates collecting information from two or more users to update at least one electronic document utilizing a multiple user independent logging in technique. Generally, electronic documents can be collected in order to create a master field list, wherein the master field list can include subsets of questions targeted for a first user or first group of users and a second user or second group of users. The master field component 102 can create such master field list with the segmented subset of questions created from the set of questions from at least one electronic document. The user segregation manager component 104 can manage the log in of users into the master field list such that each user can independently log in to a respective subset of questions for him or her. Moreover, upon receipt of information from users 202, the form aggregation component 106 can update or populate the electronic document with the information collected within the master field list.

The system 400 can be a service provided by a third-party in order to optimize completion of electronic documents, wherein a group of components 402 can be offsite from an entity (e.g., a business, a law firm, a medical practice, a dental practice, a household, a family unit, etc.). Thus, the users 202 can access a service or third-party via the Internet, a network, a website, a cloud service, etc. The users 202 can access the master field list and provide answers or information for the fill-in fields. Upon collection of such answers or information to the third-party or the service, an updated electronic document can be communicated.

In another example, the group of components 402 can be on-site to the entity (e.g., a business, a law firm, a medical practice, a dental practice, a household, a family unit, etc.). In general, the group of components 402 can be local (e.g., via WLAN, network, application, applet, installed software, etc.) to the users 202. Thus, the users 202 can provide information or answers to the master field list that correspond to at least two questions with fill-in fields from the electronic document. Upon collection of information or answers independently from users 202, the form aggregation component 106 can populate or update the electronic document with the information leveraged from the master field list.

Figure 5:
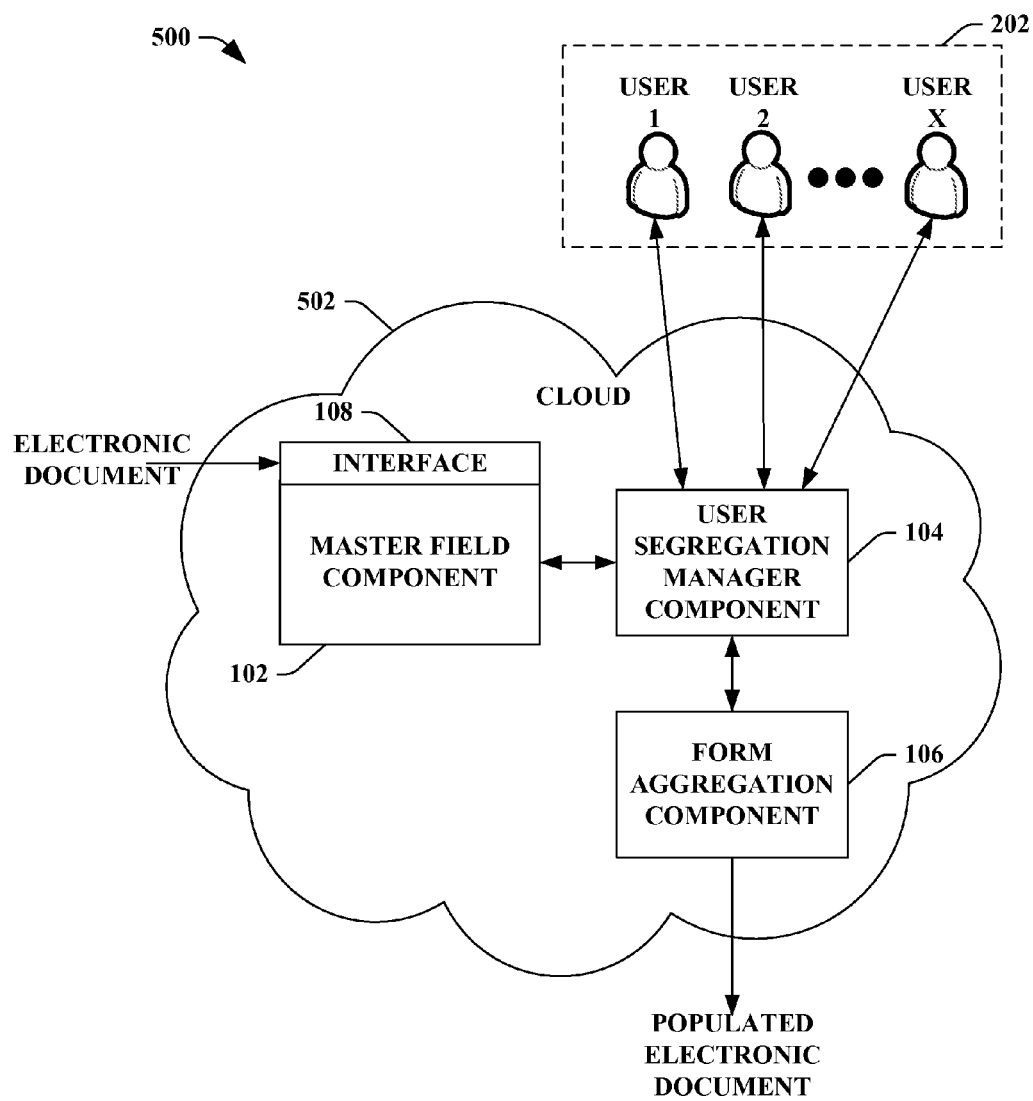
FIG. 5 illustrates a block diagram of exemplary system that facilitates updating an electronic document with multiple users logging in for subsets of respective questions from a set of questions associated with an electronic document within a cloud environment.

FIG. 5 illustrates a system 500 that facilitates updating an electronic document with multiple users logging in for subsets of respective questions from a set of questions associated with an electronic document within a cloud environment. It is to be appreciated that the system 500 can be service-based, cloud-based, distributed, monolithic, etc. The system 500 can utilize a cloud 502 that can incorporate at least one of the master field component 102, the user segregation manager component 104, the form aggregation component 106, the interface 108, the master field list, and/or any suitable combination thereof It is to be appreciated that the cloud 502 can include any suitable component, device, hardware, and/or software associated with the subject innovation. The cloud 502 can refer to any collection of resources (e.g., hardware, software, combination thereof, etc.) that are maintained by a party (e.g., off-site, on-site, third party, etc.) and accessible by an identified user over a network (e.g., Internet, wireless, LAN, cellular, Wi-Fi, WAN, etc.). The cloud 502 is intended to include any service, network service, cloud service, collection of resources, etc. and can be accessed by an identified user or users via a network.

For instance, two or more users 202 can access, join, and/or interact with the cloud 502 and, in turn, at least one of the master field component 102, the user segregation manager component 104, the form aggregation component 106, the interface 108, the master field list, and/or any suitable combination thereof. In addition, the cloud 502 can provide any suitable number of service(s) to any suitable number of user(s) and/or client(s). In particular, the cloud 502 can include resources and/or services that can allow multiple users to log in into a created master field list in order to allow each user to independently and securely provide respective information for subsets of questions, wherein the master field list includes the subset of questions from a set of questions from one or more electronic documents. Based on such multiple user log in and independent information collection, the system 500 can update or populate an electronic document by leveraging the master field list.

Figure 6:
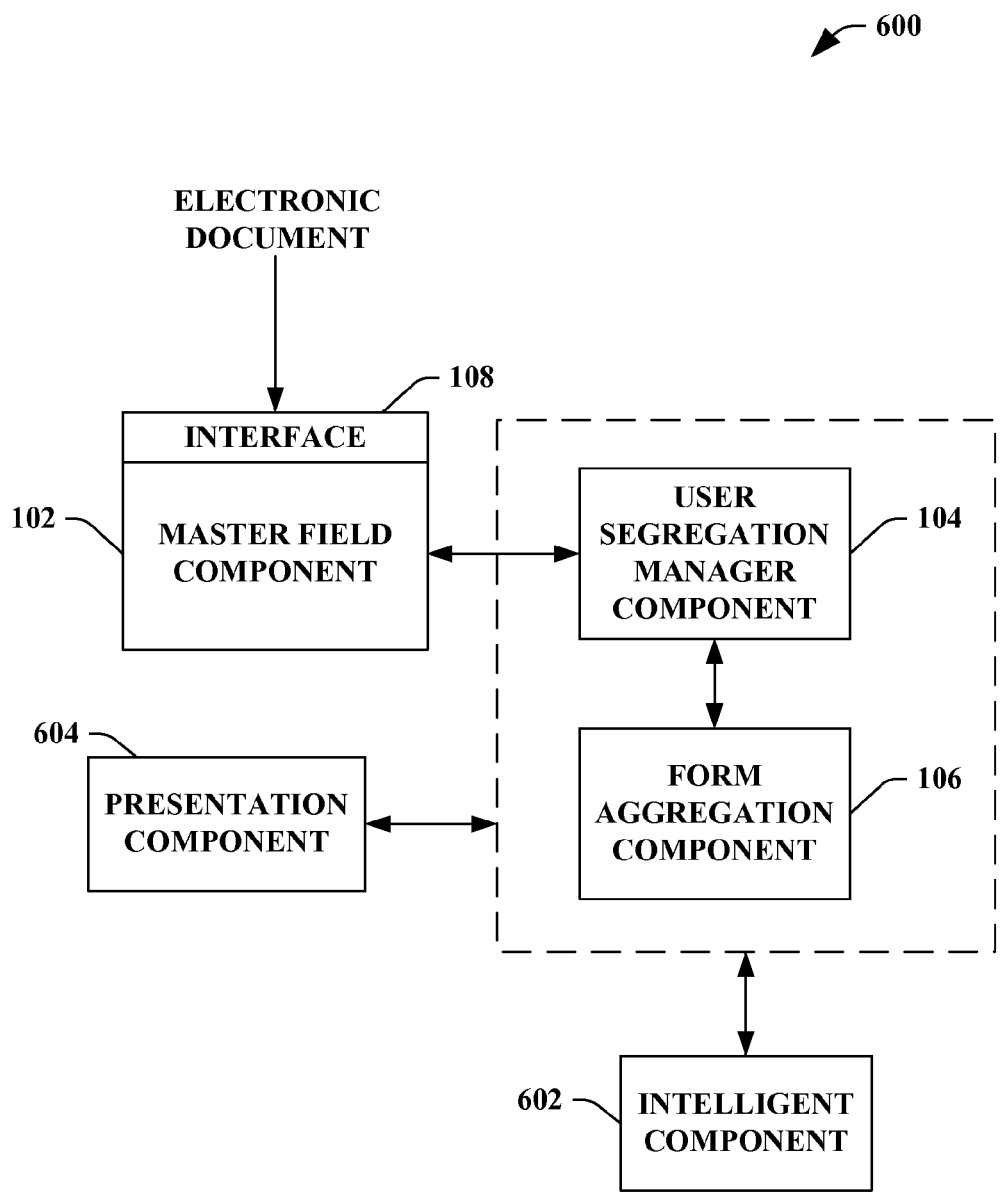
FIG. 6 illustrates a block diagram of an exemplary system that facilitates enabling multiple user logging into an electronic document for secure and independent data collection for automatic generation of a filled-in electronic document.

FIG. 6 illustrates a system 600 that employs intelligence to facilitate enabling multiple user logging into an electronic document for secure and independent data collection for automatic generation of a filled-in electronic document. The system 600 can include the master field component 102, the user segregation manager component 104, and/or the form aggregation component 106 that can be substantially similar to respective components described in previous figures. The system 600 further includes an intelligent component 602. The intelligent component 602 can be utilized by at least one of the master field component 102, the user segregation manager component 104, and/or the form aggregation component 106 to facilitate utilizing a master field list to enable two or more users to securely and independently provide information to complete or update a fill-in field on one or more electronic documents. For example, the intelligent component 602 can infer security access for two or more users, master field list segregation of questions from a set of questions related to an electronic document, answers or information to provide for a particular question and respective fill-in field related to an electronic document, notifications to communicate to users that log into the master field list, tracking or monitoring of an electronic document progress based upon the information collected via the master field list, etc.

The intelligent component 602 can employ value of information (VOI) computation in order to segment questions into subsets of questions targeted for particular users or group of users. For instance, by utilizing VOI computation, the most ideal and/or appropriate segmentation of the set of questions from an electronic document can be determined based upon the content of the question, the type of question, and/or a targeted user that is inferred to have the knowledge to answer the question. Moreover, it is to be understood that the intelligent component 602 can provide for reasoning about or infer states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines . . . ) can be employed in connection with performing automatic and/or inferred action in connection with the claimed subject matter.

A classifier is a function that maps an input attribute vector, x=(x1, x2, x3, x4, xn), to a confidence that the input belongs to a class, that is, f(x)=confidence(class). Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hypersurface in the space of possible inputs, which hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

The system 600 can further utilize a presentation component 604 that provides various types of user interfaces to facilitate interaction between a user and any component coupled to the user segregation manager component 104 and/or the form aggregation component 106. As depicted, the presentation component 604 is a separate entity that can be utilized with the user segregation manager component 104 and/or the form aggregation component 106. However, it is to be appreciated that the presentation component 604 and/or similar view components can be incorporated into the master field component 102, the user segregation manager component 104, the form aggregation component 106, and/or a stand-alone unit. The presentation component 604 can provide one or more graphical user interfaces (GUIs), command line interfaces, and the like. For example, a GUI can be rendered that provides a user with a region or means to load, import, read, etc., data, and can include a region to present the results of such. These regions can comprise known text and/or graphic regions comprising dialogue boxes, static controls, drop-down-menus, list boxes, pop-up menus, as edit controls, combo boxes, radio buttons, check boxes, push buttons, and graphic boxes. In addition, utilities to facilitate the presentation such as vertical and/or horizontal scroll bars for navigation and toolbar buttons to determine whether a region will be viewable can be employed. For example, the user can interact with one or more of the components coupled and/or incorporated into the master field component 102, the user segregation manager component 104, and/or the form aggregation component 106.

The user can also interact with the regions to select and provide information via various devices such as a mouse, a roller ball, a touchpad, a keypad, a keyboard, a touch screen, a pen and/or voice activation, a body motion detection, for example. Typically, a mechanism such as a push button or the enter key on the keyboard can be employed subsequent entering the information in order to initiate the search. However, it is to be appreciated that the claimed subject matter is not so limited. For example, merely highlighting a check box can initiate information conveyance. In another example, a command line interface can be employed. For example, the command line interface can prompt (e.g., via a text message on a display and an audio tone) the user for information via providing a text message. The user can then provide suitable information, such as alpha-numeric input corresponding to an option provided in the interface prompt or an answer to a question posed in the prompt. It is to be appreciated that the command line interface can be employed in connection with a GUI and/or API. In addition, the command line interface can be employed in connection with hardware (e.g., video cards) and/or displays (e.g., black and white, EGA, VGA, SVGA, etc.) with limited graphic support, and/or low bandwidth communication channels.

Figure 7:
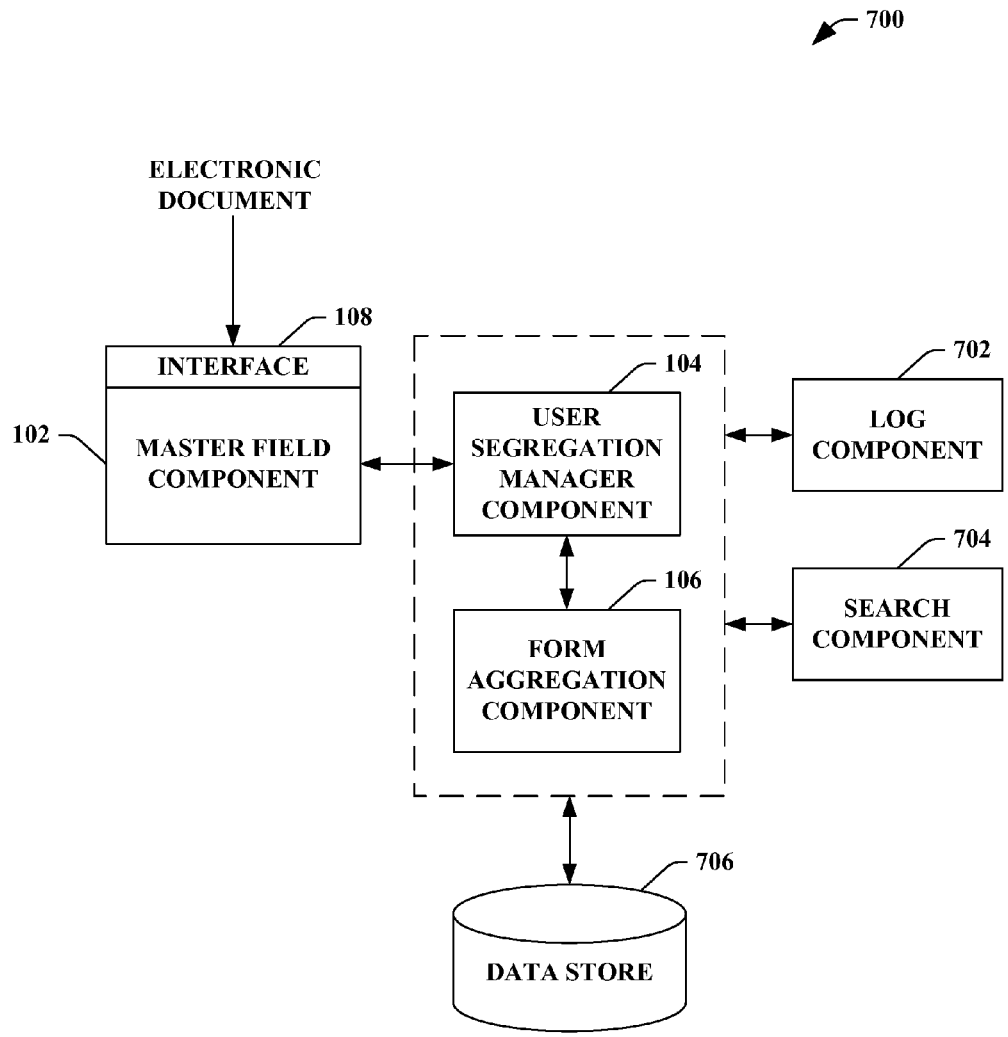
FIG. 7 illustrates a block diagram of an exemplary system that facilitates tracking and querying data related to enabling multiple users to logging in to an electronic document for updating in a secure and independent technique.

FIG. 7 illustrates a system 700 that facilitates tracking and querying data related to enabling multiple users to logging in to an electronic document for updating in a secure and independent technique. The interface 108 can receive an electronic document that can include at least two questions with respective fill-in fields that can receive a user input. The master field component 102 can create a master field list that is a collection of the questions from the one or more electronic document(s), wherein the master field list segregates the set of questions into at least a first subset of questions targeted for at first user and a second subset of questions targeted for a second user. The master field list can be managed by the user segregation manager component 104 to enable multiple user log in to facilitate collecting information for each subset of questions created, wherein each user has a respective set of questions to which he or she can provide information. The form aggregation component 106 can leverage the information collected via the master field list in order to populate or update the fill-in fields on the one or more electronic documents.

The system 700 can further include a log component 702 that can work in conjunction with the master field component 102, the user segregation manager component 104, the form aggregation component 106, the interface 108, and/or any combination thereof in order to track any data related to the system 700. For instance, the log component 702 can track and/or record data related to users that log in to the master field list, the electronic documents and respective questions utilized to create the master field list, access of the master field list from one or more users, information collected via the master field list for each user, progress of completion or update of an electronic document via the master field list, set of question segregation (e.g., number of subsets, the questions included within a subset, etc.), information related to the amount of users created and subsets created, data related to a user log in (e.g., frequency, date, time, duration, etc.), information related to electronic document(s) (e.g., type, name, description, origin of document, contents of document, etc.), and the like. Moreover, the log component 702 can track various user data in connection with most any security and/or authorization utilized with the system 700. In such a case, the log component 702 can track which particular user initiated a specific data access or communication (e.g., providing data to the master field list, etc.). In another example, the log component 702 can provide a unique identification number to electronic documents that have been updated or populated, wherein the unique identification number can be utilized to track such electronic document. For instance, a unique identification number can be assigned to a credentialing application that has been updated via the master field list and the progress of the application can be tracked by such unique identification number by the insurance company, the user(s), the entity, etc.

The system 700 can further include a search component 704 that facilitates querying data. The search component 704 can enable a user and/or machine to search data related to the system 700. Thus, the search component 704 can provide search or querying of data such as, but not limited to, information related to electronic documents (e.g., sets of questions, subset of questions derived from the set of questions, etc.), user information (e.g., names, data collected from users, etc.), user groups or types associated to a first user with the first subset of questions and a second user with the second subset of questions, answers or information collected from a user, question or fill-in field progress (e.g., identifying unanswered questions from an electronic document, master field list information collected status, etc.), etc. In addition, it is to be appreciated that the search component 704 can be utilized by any user and/or machine independent of locality and/or remotely. In other words, a remote user (e.g., on a disparate system, network, etc. from the system 700) can access the search component 704 to collect information provided for an electronic document via the master field list.

The system 700 can further include a data store 706 that can include any suitable data related to the master field component 102, the user segregation manager component 104, the form aggregation component 106, the interface 108, etc. For example, the data store 706 can store data such as, but not limited to, information related to electronic documents (e.g., sets of questions, subset of questions derived from the set of questions, type, name, description, origin of document, contents of document, etc.), user information (e.g., names, data collected from users, etc.), user groups or types associated to a first user with the first subset of questions and a second user with the second subset of questions, answers or information collected from a user, question or fill-in field progress (e.g., identifying unanswered questions from an electronic document, master field list information collected status, etc.), etc.

It is to be appreciated that the data store 706 can be, for example, either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable programmable ROM (EEPROM), or flash memory. Volatile memory can include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), Rambus direct RAM (RDRAM), direct Rambus dynamic RAM (DRDRAM), and Rambus dynamic RAM (RDRAM). The data store 706 of the subject systems and methods is intended to comprise, without being limited to, these and any other suitable types of memory. In addition, it is to be appreciated that the data store 706 can be a server, a database, a hard drive, a pen drive, an external hard drive, a portable hard drive, and the like.

Figure 8:
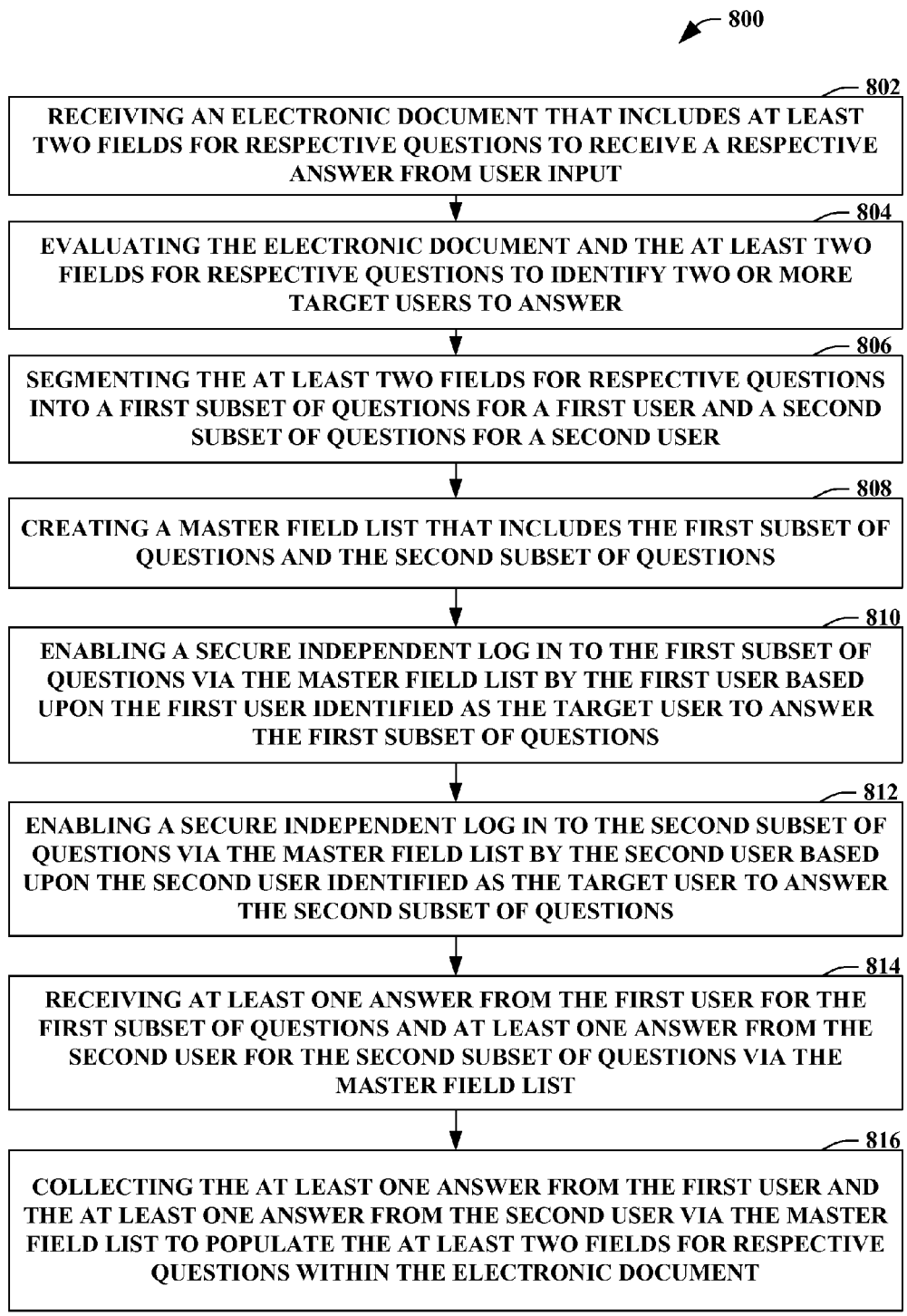
FIG. 8 illustrates an exemplary methodology for enabling multiple user logging into an electronic document for secure and independent data collection for automatic generation of a filled-in electronic document.
Figure 9:
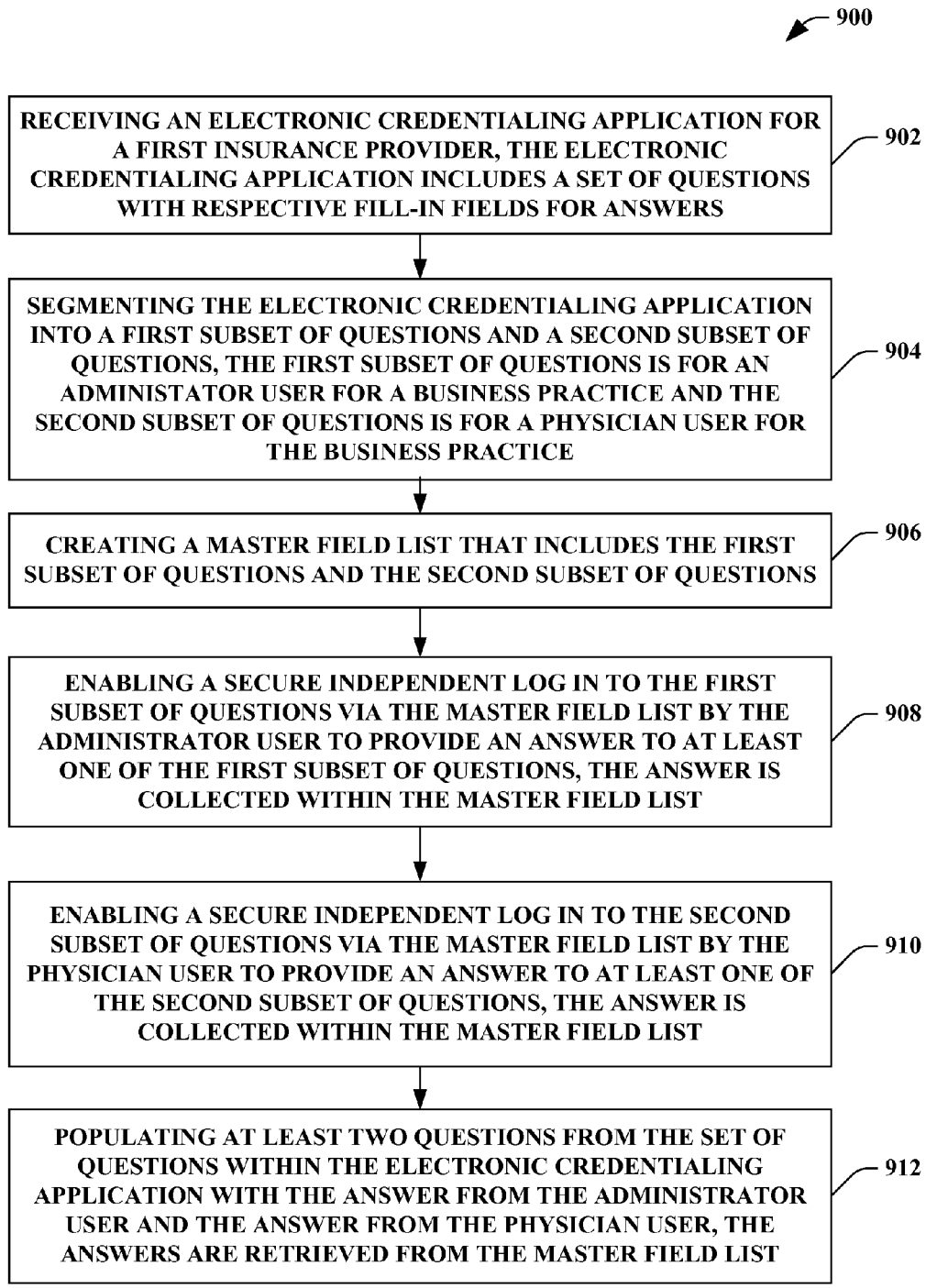
FIG. 9 illustrates an exemplary methodology for two or more users to provide independent information for respective questions from an electronic credentialing application for an insurance provider.
Figure 10:
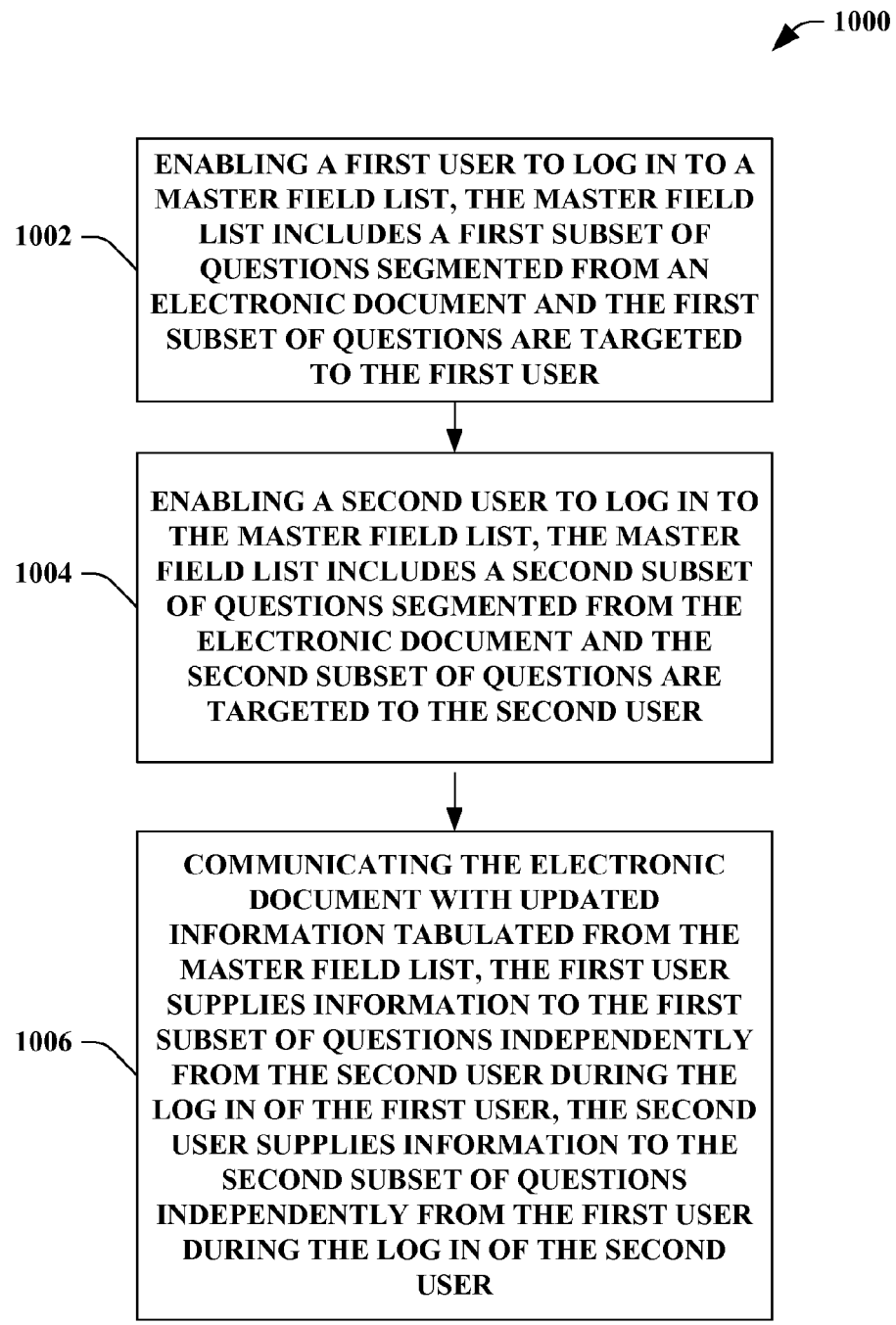
FIG. 10 illustrates an exemplary methodology that facilitates implementing a multiple user log in to a master field list for independent and secure information collection for an electronic document.

FIGS. 8-10 illustrate methodologies and/or flow diagrams in accordance with the claimed subject matter. For simplicity of explanation, the methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts may be required to implement the methodologies in accordance with the claimed subject matter. In addition, those skilled in the art will understand and appreciate that the methodologies could alternatively be represented as a series of interrelated states via a state diagram or events. Additionally, it should be further appreciated that the methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device, carrier, or media.

FIG. 8 illustrates a methodology 800 for enabling multiple user logging into an electronic document for secure and independent data collection for automatic generation of a filled-in electronic document. At reference numeral 802, an electronic document that includes at least two fields for respective questions to receive a respective answer from a user input can be received. The electronic document can be, for instance, an electronic application, a digital form, an electronic questionnaire, a college application, a business application for credit at a bank, a credentialing application for a medical practice, a credentialing application for a dental practice, a business lease agreement, a credit card application for a business, a group medical insurance application for a business, a loan application, a student loan application, an electronic evaluation form, etc. At reference numeral 804, the electronic document and the at least two field for respective questions to identify two or more target users to answer can be evaluated. At reference numeral 806, the at least two field for respective questions can be segmented into a first subset of questions for a first user or first group of users and a second subset of questions for a second user or second group of users. At reference numeral 808, a master field list can be created that includes the first subset of questions and the second subset of questions.

At reference numeral 810, a secure independent log in can be enabled to the first subset of questions via the master field list by the first user based upon the first user identified as the target user to answer the first subset of questions. At reference numeral 812, a secure independent log in can be enabled to the second subset of questions via the master field list by the second user based upon the second user identified as the target user to answer the second subset of questions. At reference numeral 814, at least one answer from the first user for the first subset of questions and at least one answer from the second user for the second subset of questions can be received via the master field list. At reference numeral 816, the at least one answer from the first user and the at least one answer from the second user can be collected via the master field list to populate the at least two fields for respective questions within the electronic document.

FIG. 9 illustrates a methodology 900 for two or more users to provide independent information for respective questions from an electronic credentialing application for an insurance provider. At reference numeral 902, an electronic credentialing application for a first insurance provider can be received, wherein the electronic credentialing application includes a set of questions with respective fill-in fields for answers. At reference numeral 904, the electronic credentialing application can be segmented into a first subset of questions and a second subset of questions, wherein the first subset of questions is for an administrator user for a business practice and the second subset of questions is for a physician user for the business practice. For example, the administrator user can be any user that has knowledge about a business practice, medical practice, or dental practice such as, but not limited to, office location, credentialing application contact information, staff or business office contact information, billing information, payment information, accessibility of the office information, services for the office, insurance information, professional liability insurance information, information not known to a physician user, etc. Moreover, the physician user can be any user that has knowledge about his or her education or employment history such as, but not limited to resume information, medical/dental expertise, employers, professional identifications, board certifications, state licenses, training information, internship/residency information, fellowship information, specialty information, certifications, office hours of work, partners/associates, mid-level practitioners, hospital privileges, disclosure questions, etc. At reference numeral 906, a master field list can be created that includes the first subset of questions and the second subset of questions.

At reference numeral 908, a secure independent log in to the first subset of questions can be enabled via the master field list by the administrator user to provide an answer to at least one of the first subset of questions, wherein the answer is collected within the master field list. At reference numeral 910, a secure independent log in to the second subset of questions can be enabled via the master field list by the physician user to provide an answer to at least one of the second subset of questions, wherein the answer is collected within the master field list. At reference numeral 912, at least two questions from the set of questions within the electronic credentialing application can be populated with the answer from the administrator user and the answer from the physician user, wherein the answers are retrieved from the master field list.

FIG. 10 illustrates a methodology 1000 that facilitates implementing a multiple user log in to a master field list for independent and secure information collection for an electronic document. At reference numeral 1002, a first user can be enabled to log in to a master field list, the master field list includes a first subset of questions segmented from an electronic document and the first subset of questions are targeted to the first user. At reference numeral 1004, a second user can be enabled to log in to the master field list, the master field list includes a second subset of questions segmented from the electronic document and the second subset of questions are targeted to the second user. At reference numeral 1006, the electronic document can be communicated with updated information tabulated from the master field list, the first user supplied information to the first subset of questions independently from the second user during the log in of the first user, the second user supplies information to the second subset of questions independently from the first user during the log in of the second user.

Figure 11:
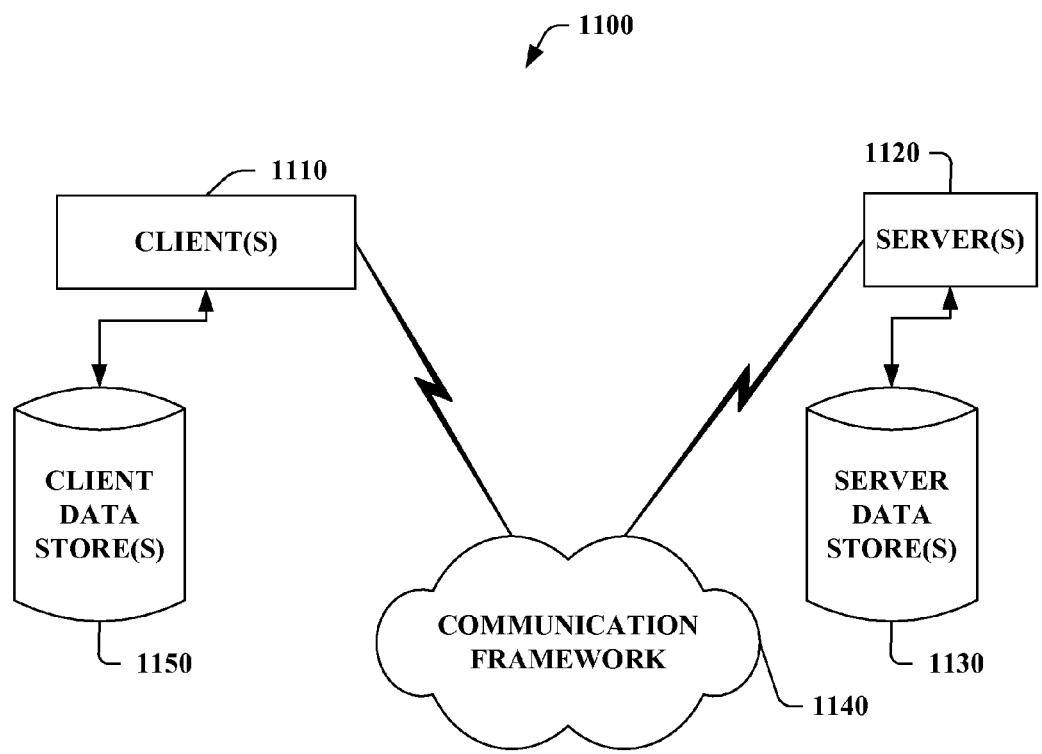
FIG. 11 illustrates an exemplary networking environment, wherein aspects of the claimed subject matter can be employed.
Figure 12:
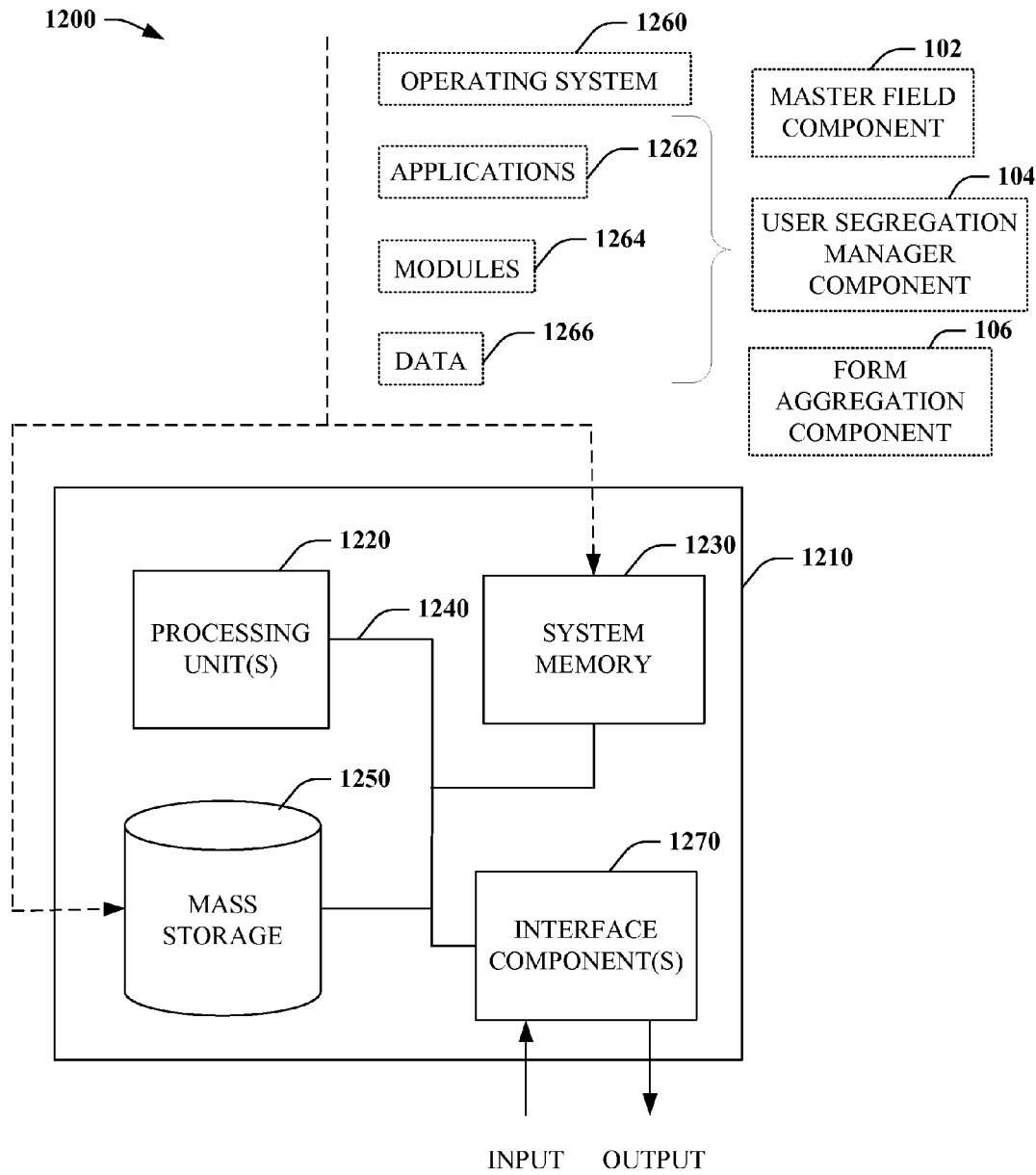
FIG. 12 illustrates an exemplary operating environment that can be employed in accordance with the claimed subject matter.

In order to provide a context for the claimed subject matter, FIG. 11 and FIG. 12 as well as the following discussion are intended to provide a brief, general description of a suitable environment in which various aspects of the subject matter can be implemented. The suitable environment, however, is only an example and is not intended to suggest any limitation as to scope of use or functionality.

While the above disclosed system and methods can be described in the general context of computer-executable instructions of a program that runs on one or more computers, those skilled in the art will recognize that aspects can also be implemented in combination with other program modules or the like. Generally, program modules include routines, programs, components, data structures, among other things that perform particular tasks and/or implement particular abstract data types. Moreover, those skilled in the art will appreciate that the above systems and methods can be practiced with various computer system configurations, including single-processor, multi-processor or multi-core processor computer systems, mini-computing devices, mainframe computers, as well as personal computers, hand-held computing devices (e.g., personal digital assistant (PDA), phone, watch . . . ), microprocessor-based or programmable consumer or industrial electronics, and the like. Aspects can also be practiced in distributed computing environments where tasks are performed by remote processing devices that are linked through a communications network. However, some, if not all aspects of the claimed subject matter can be practiced on stand-alone computers. In a distributed computing environment, program modules may be located in one or both of local and remote memory storage devices.

FIG. 11 is a schematic block diagram of a sample-computing environment 1100 with which the claimed subject matter can interact. The system 1100 can include one or more client (s) 1110. The one or more client(s) 1110 can be hardware and/or software (e.g., threads, processes, computing devices, computing devices utilizing a cloud network or system, etc.). The system 1100 also can include one or more server(s) 1120. The server(s) 1120 can be hardware and/or software (e.g., threads, processes, computing devices, computing devices utilizing a cloud network or system, etc.). One possible communication between a client 1110 and a server 1120 can be in the form of a data packet adapted to be transmitted between two or more computer processes. The system 1100 includes a communication framework 1140 that can be employed to facilitate communications between the client(s) 1110 and the server(s) 1120. The client(s) 1110 are physically or wirelessly connected to one or more client data store(s) 1150 that can be employed to store information local to the client(s) 1110. Similarly, the server(s) 1120 are physically or wirelessly connected to one or more server data store(s) 1130 that can be employed to store information local to the servers 1120. In other words, the server(s) 1120 can communicate with the client(s) 1110 via the communications network 1140 in order to exchange data, information, and the like.

With reference to FIG. 12, illustrated is an example computer or computing device 1210 (e.g., desktop, laptop, server, hand-held, programmable consumer or industrial electronics, set-top box, game system . . . ). The computer 1210 includes one or more processing units or processors 1220, system memory 1230, system bus 1240, mass storage 1250, and one or more interface components 1270. The system bus 1240 communicatively couples at least the above system components. However, it is to be appreciated that in its simplest form the computer 1210 can include one or more processors 1220 coupled to system memory 1230 that execute various computer executable actions, instructions, and or components.

The processing unit 1220 can be implemented with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any processor, controller, microcontroller, or state machine. The processing unit 1220 may also be implemented as a combination of computing devices, for example a combination of a DSP and a microprocessor, a plurality of microprocessors, multi-core processors, one or more microprocessors in conjunction with a DSP core, or any other such configuration.

The computer 1210 can include or otherwise interact with a variety of computer-readable media to facilitate control of the computer 1210 to implement one or more aspects of the claimed subject matter. The computer-readable media can be any available media that can be accessed by the computer 1210 and includes volatile and nonvolatile media and removable and non-removable media. By way of example, and not limitation, computer-readable media may comprise computer storage media and communication media.

Computer storage media includes volatile and nonvolatile, removable and non-removable media implemented in any method or technology for storage of information such as computer-readable instructions, data structures, program modules, or other data. Computer storage media includes, but is not limited to memory devices (e.g., random access memory (RAM), read-only memory (ROM), electrically erasable programmable read-only memory (EEPROM) . . . ), magnetic storage devices (e.g., hard disk, floppy disk, cassettes, tape . . . ), optical disks (e.g., compact disk (CD), digital versatile disk (DVD) . . . ), and solid state devices (e.g., solid state drive (SSD), flash memory drive (e.g., card, stick, key drive . . . ) . . . ), or any other medium which can be used to store the desired information and which can be accessed by the computer 1210.

Communication media typically embodies computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

System memory 1230 and mass storage 1250 are examples of computer-readable storage media. Depending on the exact configuration and type of computing device, system memory 1230 may be volatile (e.g., RAM), non-volatile (e.g., ROM, flash memory . . . ) or some combination of the two. By way of example, the basic input/output system (BIOS), including basic routines to transfer information between elements within the computer 1210, such as during start-up, can be stored in nonvolatile memory, while volatile memory can act as external cache memory to facilitate processing by the processing unit 1220, among other things.

Mass storage 1250 includes removable/non-removable, volatile/non-volatile computer storage media for storage of large amounts of data relative to the system memory 1230. For example, mass storage 1250 includes, but is not limited to, one or more devices such as a magnetic or optical disk drive, floppy disk drive, flash memory, solid-state drive, or memory stick.

System memory 1230 and mass storage 1250 can include or have stored therein operating system 1260, one or more applications 1262, one or more program modules 1264, and data 1266. The operating system 1260 acts to control and allocate resources of the computer 1210. Applications 1262 include one or both of system and application software and can leverage management of resources by operating system 1260 through program modules 1264 and data 1266 stored in system memory 1230 and/or mass storage 1250 to perform one or more actions. Accordingly, applications 1262 can turn a general-purpose computer 1210 into a specialized machine in accordance with the logic provided thereby.

All or portions of the claimed subject matter can be implemented using standard programming and/or engineering techniques to produce software, firmware, hardware, or any combination thereof to control a computer to realize the disclosed functionality. By way of example and not limitation, the master field component 102, the user segregation manager component 104, and/or the form aggregation component 106 can be utilized within or incorporated into the applications 1264 and/or the modules 1266. For instance, the system 100 can be employed as a plug-in module utilizing the module 1266 or as an application. In general, the master field component 102, the user segregation manager component 104, and/or the form aggregation component 106 can be employed with the system 1200.

The computer 1210 also includes one or more interface components 1270 that are communicatively coupled to the system bus 1240 and facilitate interaction with the computer 1210. By way of example, the interface component 1270 can be a port (e.g., serial, parallel, PCMCIA, USB, FireWire . . . ) or an interface card (e.g., sound, video . . . ) or the like. In one example implementation, the interface component 1270 can be embodied as a user input/output interface to enable a user to enter commands and information into the computer 1210 through one or more input devices (e.g., pointing device such as a mouse, trackball, stylus, touch pad, keyboard, microphone, joystick, game pad, satellite dish, scanner, camera, other computer . . . ). In another example implementation, the interface component 1270 can be embodied as an output peripheral interface to supply output to displays (e.g., CRT, LCD, plasma . . . ), speakers, printers, and/or other computers, among other things. Still further yet, the interface component 1270 can be embodied as a network interface to enable communication with other computing devices (not shown), such as over a wired or wireless communications link.

What has been described above includes examples of the subject innovation. It is, of course, not possible to describe every conceivable combination of components or methodologies for purposes of describing the claimed subject matter, but one of ordinary skill in the art may recognize that many further combinations and permutations of the subject innovation are possible. Accordingly, the claimed subject matter is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable medium having computer-executable instructions for performing the acts and/or events of the various methods of the claimed subject matter.

There are multiple ways of implementing the present innovation, e.g., an appropriate API, tool kit, driver code, operating system, control, standalone or downloadable software object, etc. which enables applications and services to use the advertising techniques of the invention. The claimed subject matter contemplates the use from the standpoint of an API (or other software object), as well as from a software or hardware object that operates according to the advertising techniques in accordance with the invention. Thus, various implementations of the innovation described herein may have aspects that are wholly in hardware, partly in hardware and partly in software, as well as in software.

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but generally known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

What is claimed is:

1. A computer-implemented system that facilitates completing multiple electronic document applications, comprising:
   a first entity that includes at least one administrator user and at least one medical professional user;
   an interface component to receive two or more electronic documents, wherein each electronic document includes at least two or more questions with respective fill-in fields to be completed by a user input;
   a master field component that evaluates the two or more electronic documents to segment the two or more questions with respective fill-in fields into a first subset of questions and a second subset of questions to create a master field list,
      wherein the master field list is a compilation of the two or more questions with respective fill-in fields from the two or more electronic documents, and
      wherein the first subset of questions are stored for response from the at least one administrator user to answer and the second subset of questions are stored for response from the at least one medical professional user to answer;
   a user segregation manager component that concurrently validates each of the administrator user in the first entity and the at least one medical professional user in the first entity to the master field list in which information is collected separately within the master field list, the administrator user provides information for the first subset of questions and the at least one medical professional provides information for the second subset of questions;
   a form aggregation component that utilizes the master field list to populate the two or more electronic documents and the respective fill-in fields to include information aggregated from the administrator user and the at least one medical professional user;
   a memory; and
   a processor coupled to the memory.

2. The computer-implemented system of claim 1, further comprising:
   the first entity includes two or more medical professional users; and
   the master field component creates one or more copied subsets of questions,
   wherein the one or more copied subsets of questions are a copy of the second subset of questions for each of the two or more medical professional users,
   wherein the one or more copied subsets enable each of the two or more medical professional users to concurrently access the master field list to provide information responsive to the second subset of questions, and
   wherein the second subset of questions and one or more copied subsets persist in two or more storage locations on the memory.

3. The computer-implemented system of claim 2, further comprising a security engine that enables secure data communication such that the following is employed:
   an administrator user log in to the master field list to at least one of review or edit information related to the first subset of questions;
   an administrator user log in to the master field list to review information provided by each of the two or more medical professional users within the second subset of questions; and
   each of the two or more medical professional users independently log in to the master field list to provide information, wherein information provided by one of the two or more medical professional users is secure from another medical professional user.

4. The computer-implemented system of claim 2, further comprising:
   a second entity that includes at least one administrator user and at least one medical professional user;
   the master field component creates a first copied subset, wherein the first copied subset is a copy of the first subset of questions within the master field list for each administrator user within each of the first entity and the second entity;
   the master field component creates a second copied subset, wherein the second copied subset is a copy of the second subset of questions within the master field list for each medical professional user within each of the first entity and the second entity;
   a user segregation manager component that enables each of the administrator user in the first entity or the second entity and the at least one medical professional user in the first entity or the second entity to independently log in to the master field list in which information is collected separately within the master field list, the administrator user from the first entity provides information for the first copied subset, the administrator user from the second entity provides information for the first copied subset, the at least one medical professional user from the first entity provides information for the second copied subset, and the at least one medical professional user from the second entity provides information for the second copied subset;

a form aggregation component that utilizes the master field list to populate the two or more electronic documents and the respective fill-in fields for at least one of the first entity or the second entity, wherein population of the two or more electronic documents includes information aggregated from at least one of the following:

at least one administrator user from the first entity and at least one medical professional user from the first entity; or at least one administrator user from the second entity and the at least one medical professional user from the second entity.

5. The computer-implemented system of claim 2, the electronic document is a region-based credentialing application from at least one of a medical insurance company or a dental insurance company, wherein 1) the medical insurance company provides insurance coverage to a patient in which such region-based credentialing application enables a medical physician to accept such insurance coverage for patients, and 2) the dental insurance company provides insurance coverage to a patient in which such region-based credentialing application enables a dental physician to accept such insurance coverage for patients.

6. The computer-implemented system of claim 2, further comprising:

the first entity is at least one of a medical practice or a dentistry practice, the at least one medical professional user is at least one of a doctor or a dentist;

the administrator user is an employee with the first entity that handles administrative duties related to at least one of the medical practice or the dentistry practice.

7. A system that facilitates generating completed electronic document forms from multiple users, comprising:

an interface component that receives an electronic document that includes a set of questions and a respective set of fill-in fields, wherein the respective set of fill-in fields receive an answer to each respective question in the set of questions;

a master field component that creates a master field list that segregates the set of questions and the respective set of fill-in fields into a first subset of questions and a second subset of questions, wherein the first subset of questions are restricted to a first user for input associated with the first subset of questions and the second subset of questions are restricted to a second user for input associated with the second subset of questions;

a user segregation manager component that enables the following:

the first user to access at least one question and to transmit an answer to at least one question within the first subset of questions independent of the second user and the second subset of questions, the answer is stored to the master field list; and the second user to access at least one question and to transmit an answer to at least one question within the second subset of questions independent of the first user and the first subset of questions, the answer is stored to the master field list;

the user segregation manager component employs secure data communication between the first user and the master field list and the second user and the master field list such that information communicated by the first user and the master field list is isolated from the second user and the information communicated by the second user and the master field list is isolated from the first user;

a form aggregation component that leverages the master field list to collect information received from the first user related to the first subset of questions and information received from the second user related to the second subset of questions to update the set of questions and the respective set of fill-in fields on the electronic document;

a memory; and a processor coupled to the memory.

8. The system of claim 7, further comprising:

the master field component segregates the set of questions and the respective set of fill-in fields into a third subset of questions targeted to a third user;

the user segregation manager component enables the following:

the third user to review at least one answer stored in the master field list from at least one of the first user, the second user, or the third user; and the third user to transmit an answer to at least one question within the third subset of questions independent of the first user and the first subset of questions, the second user and the second subset of questions, the answer is stored to the master field list;

the user segregation manager component employs secure data communication between the third user and the master field list such that information communicated by the third user and the master field list is isolated from the first user and the second user; and the form aggregation component that leverages the master field list to collect information received from the first user related to the first subset of questions, information received from the second user related to the second subset of questions, and information received from the third user related to the third subset of questions to update the set of questions and the respective set of fill-in fields on the electronic document.

9. The system of claim 8, the electronic document is a region-based credentialing application from at least one of a medical insurance company or a dental insurance company.

10. The system of claim 8, the first user is at least one of a doctor or a dentist, the second user is at least one of a doctor or a dentist, and the third user is an administrator for at least one of a medical practice or a dentistry practice.

11. The system of claim 7, further comprising the interface component receives two or more electronic documents that each include a set of questions and a respective set of fill-in fields, wherein the respective set of fill-in fields, for each of the two or more electronic documents, receive an answer to each respective question in the set of questions.

12. The system of claim 11, further comprising:

the master field component creates the master field list for two or more electronic documents in which the master field list segregates the set of questions and the respective set of fill-in fields for the two or more electronic documents; and the form aggregation component leverages the master field list for two or more electronic documents to collect information received to update the set of questions and the respective set of fill-in fields on the two or more electronic documents.

13. The system of claim 12, the form aggregation component populates each of the two or more electronic documents with at least one answer stored in the master field list, wherein the two or more electronic documents are updated with information stored in the master field list from at least one of the first user, the second user, or a third user.

14. The system of claim 7, the electronic document is at least one of an electronic application, a digital form, an electronic questionnaire, a college application, a business application for credit at a bank, a credentialing application for a medical practice, a credentialing application for a dental practice, a business lease agreement, a credit card application for a business, a group medical insurance application for a business, a loan application, a student loan application, or an electronic evaluation form.

15. The system of claim 7, further comprising:
the first user is at least one of an administrative user, a first parent, a parent user, a professional user, a teacher, a professor user, or a borrower; and
the second user is at least one of a medical professional user, a second parent, a child user, a professional assistant user, a student user, or a co-signer user.

16. The system of claim 7, further comprising a notification component that communicates a notification based upon at least one of a progress of answering questions within the master field list, a duration of time, a deadline, an availability of a master field list to access, or a user request.

17. The system of claim 16, the notification is at least one of an email, a short message service (SMS), a text message, a phone call, a video call, a cellular call, a page, a message to a social network, a message to a website, or a message to an automated telephone service.

18. A computer-implemented method that facilitates generating completed electronic document forms from multiple users, comprising:
receiving an electronic document that includes at least two fields for respective questions to receive a respective answer from user input;
evaluating the electronic document and the at least two fields for respective questions to identify two or more target users to answer;
segmenting the at least two fields for respective questions into a first subset of questions for response from a first user and a second subset of questions for response from a second user;
creating a master field list that includes the first subset of questions and the second subset of questions;
providing a secure concurrent log in interface providing access to the first subset of questions and the second subset of questions for at least the first user and the second user based on user permissions associated with the two or more users;
wherein the first user possessing permissions to answer the first subset of questions is logged into the first subset of questions, and
wherein the second user possessing permissions to answer the second subset of questions is logged into the second subset of questions;
providing an answer entry interface to at least the first user and the second user, wherein the answer interface presents the first subset of questions to the first user and the second subset of questions to the second user;
receiving at least one answer from the first user for the first subset of questions and at least one answer from the second user for the second subset of questions via the master field list; and
populating the at least two fields within the electronic document from information within the master field list based at least in part on the at least one answer from the first user for the first subset of questions and the at least one answer from the second user for the second subset of questions.

19. The method of claim 18, the electronic document is at least one of an electronic application, a digital form, an electronic questionnaire, a college application, a business application for credit at a bank, a credentialing application for a medical practice, a credentialing application for a dental practice, a business lease agreement, a credit card application for a business, a group medical insurance application for a business, a loan application, a student loan application, or an electronic evaluation form.

20. The method of claim 18, further comprising the electronic document is a region-based credentialing application and the first user is an administrator user and the second user is a physician user.

* * * * *